US006709561B1

United States Patent
Pavlov et al.

(10) Patent No.: US 6,709,561 B1
(45) Date of Patent: Mar. 23, 2004

(54) MEASUREMENT OF THE CONCENTRATION OF A REDUCING AGENT IN AN ELECTROLESS PLATING BATH

(75) Inventors: Michael Pavlov, Fairlawn, NJ (US); Gene Chalyt, Washington Township, NJ (US); Peter Bratin, Flushing, NY (US); Alex Kogan, Carlstadt, NJ (US); Michael James Perpich, Hackensack, NJ (US)

(73) Assignee: ECI Technology, Inc., East Rutherford, NJ (US)

( * ) Notice: Subject to any disclaimer, the term of this patent is extended or adjusted under 35 U.S.C. 154(b) by 0 days.

(21) Appl. No.: 10/288,989

(22) Filed: Nov. 6, 2002

(51) Int. Cl.[7] .............................................. C25D 21/12
(52) U.S. Cl. ..................... 205/81; 205/775; 205/780.5; 205/787; 205/793.5; 205/794
(58) Field of Search ..................... 205/81, 775, 780.5, 205/787, 793.5, 794

(56) References Cited

U.S. PATENT DOCUMENTS

| 4,654,126 A | * | 3/1987 | Amelio et al. | ............... | 205/794 |
| 6,572,753 B2 | * | 6/2003 | Chalyt et al. | ................. | 205/81 |

* cited by examiner

*Primary Examiner*—Robert R. Koehler
(74) *Attorney, Agent, or Firm*—D. Morgan Tench

(57) ABSTRACT

The concentration of a reducing agent in an electroless bath for plating a first metal is determined from the effect of the reducing agent on the electrodeposition rate of a second metal. For electroless cobalt and nickel baths, a sample of the electroless plating bath is added to an acid copper plating solution and the copper electrodeposition rate is measured by cyclic voltammetric stripping (CVS) analysis. Separate analyses for hypophosphite and dimethylamineborane in baths employing both reducing agents are attained via selective decomposition of the dimethylamineborane in acidic solution.

28 Claims, 2 Drawing Sheets

MEASUREMENT OF THE CONCENTRATION OF A REDUCING AGENT IN AN ELECTROLESS PLATING BATH

CROSS-REFERENCE TO RELATED APPLICATIONS

This application is related to U.S. patent application Ser. No. 09/968,202, filed Oct. 1, 2001, to Chalyt et al., now U.S. Pat. No. 6,572,753, which is assigned to the same assignee. The teachings of this patent application are incorporated herein by reference.

BACKGROUND OF THE INVENTION

1. Field of the Invention

This invention is concerned with analysis of reducing agents in electroless plating baths as a means of providing control over the deposit properties.

2. Description of the Related Art

Plating baths are widely used by the electronics industry to deposit a variety of metals (copper, nickel and gold, for example) on various parts, including circuit boards, semiconductor chips, and device packages. Both electroplating baths and electroless plating baths are employed. For electroplating, the part and a counter electrode are brought into contact with the electroplating bath containing ions of an electrodepositable metal, and the metal is electrodeposited by applying a negative potential to the part relative to the counter electrode. For electroless plating, the bath also contains a reducing agent which, in the presence of a catalyst, chemically reduces the metal ions to form a deposit of the metal. Since the deposited metal itself may serve as the catalyst, the electroless deposition, once initiated, proceeds without the need for an externally applied potential.

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions, for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in the plating bath between fixed potential limits so that metal is alternately plated on and stripped from the electrode surface. Such potential cycling is designed to establish a steady state for the electrode surface so that reproducible results are obtained. Accumulation of organic films or other contaminants on the electrode surface can be avoided by periodically cycling the potential of the electrode in the plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52 (1981) and Plating Surf. Fin. 69(3), 62 (1982)].

Acid copper sulfate baths are employed in the "Damascene" process (e.g., P. C. Andricacos, Electrochem. Soc. Interface, Spring 1999, p.32; U.S. Pat. No. 4,789,648 to Chow et al.; U.S. Pat. No. 5,209,817 to Ahmad et al.) to electrodeposit copper within fine trenches and vias in dielectric material on semiconductor chips. CVS methods for controlling the three organic additives in acid copper baths needed for plating ultra-fine Damascene features are described in U.S. patent application Ser. No. 09/968,202 to Chalyt et al. (filed Oct. 1, 2001), now U.S. Pat. No. 6,572,753. In the Damascene process, as currently practiced, vias and trenches are etched in the chip's dielectric material, which is typically silicon dioxide, although materials with lower dielectric constants are under development. A barrier layer, e.g., titanium nitride (TiN), tantalum nitride (TaN) or tungsten nitride ($WN_x$), is deposited on the sidewalls and bottoms of the trenches and vias, typically by reactive sputtering, to prevent Cu migration into the dielectric material and degradation of the device performance. Over the barrier layer, a thin copper seed layer is deposited, typically by sputtering, to provide enhanced conductivity and good adhesion. Copper is then electrodeposited into the trenches and vias. Copper deposited on the outer surface, i.e., outside of the trenches and vias, is removed by chemical mechanical polishing (CMP). A capping or cladding layer (e.g., TiN, TaN or $WN_x$) is applied to the exposed copper circuitry to suppress oxidation and migration of the copper. The "Dual Damascene" process involves deposition in both trenches and vias at the same time. In this document, the term "Damascene" also encompasses the "Dual Damascene" process.

Damascene barrier layers based on electrolessly deposited cobalt and nickel are currently under investigation [e.g., Kohn et al., Mater. Sci. Eng. A302, 18 (2001)]. Such metallic materials have higher electrical conductivities compared to metal nitride barrier materials, which enables copper to be electrodeposited directly on the barrier layer without the use of a copper seed layer. Higher barrier layer conductivity also reduces the overall resistance for circuit traces of a given cross-sectional area. In addition, electroless deposition provides, highly conformal coatings, even within ultra-fine trenches and vias, so that the overall coating thickness can be minimized. Electroless cobalt and nickel baths being investigated for Damascene barrier deposition typically also contain a refractory metal (e.g., tungsten, molybdenum or rhenium), which co-deposits with the cobalt or nickel and increases the maximum temperature at which effective barrier properties are retained.

For electroless cobalt and nickel baths, hypophosphite ($H_2PO_2$) is typically used as the reducing agent, which introduces phosphorus into the deposit. The codeposited phosphorus reduces the deposit grain size and crystallinity (compared to electrodeposits), which tends to improve the deposit barrier properties. Alternative reducing agents include the boranes, dimethylamineborane (DMAB), for example. Use of a borane reducing agent introduces boron into the deposit. A typical bath for electroless deposition of Damascene barrier layers comprises 0.1 M cobalt chloride or sulfate, 0.2 M sodium hypophosphite, 0.03 M sodium tungstate, 0.5 M sodium citrate, 0.5 M boric acid, and a small amount of a surfactant. Such Co(W,P) baths typically operate at about pH 9 and a temperature of 85°–95° C., and may also contain organic additives.

For electroless deposition of cobalt and nickel on dielectric materials, such as silicon oxide, or on metals that are not sufficiently catalytic for the electroless process, such as copper, a seed layer of a catalytic metal is generally employed. Typically, catalytic palladium is deposited by immersion of the part in an acidic activator solution containing palladium chloride and fluoride ion. The fluoride ion tends to cause dissolution of surface oxides on the substrate so that a displacement layer of palladium is formed. Alternatively, a seed layer of the electrolessly deposited metal, cobalt or nickel, may be applied by sputtering.

Recently, direct deposition of capping layers of Co(W,P) on Damascene copper circuits was reported (T. Itabashi, N. Nakano and H. Akahoshi, Proc. IITC 2002, p. 285–287) for a Co(W,P) bath employing two reducing agents. In this case, electroless deposition is initiated by the more active reducing agent (DMAB), which is present at a relatively low concentration. As the DMAB reducing agent becomes depleted at the part surface, electroless deposition is sustained by the less active reducing agent (hypophosphite), which provides better deposit properties.

Close control of the concentrations of reducing agents in electroless plating baths is necessary to provide acceptable deposit properties but available reducing agent analysis methods are cumbersome and inadequate. In a typical prior art method, the reducing agent in a plating bath sample is first fully oxidized in an acidic solution by addition of excess iodine. This oxidation reaction requires about 30 minutes and must be performed in the absence of light. The excess iodine in the acidic solution is then back-titrated with a solution containing thiosulfate ion, typically using loss of solution color as the titration endpoint. Such prior art methods do not provide analysis results within the time frame needed for close control of the reducing agent, and are not amenable to automated on-line bath control.

SUMMARY OF THE INVENTION

This invention provides a method for determining the concentration of a reducing agent in an electroless plating bath from the increase produced by the reducing agent in the electrodeposition rate of a metal. The metal electrodeposition rate is measured for a test solution comprising an electrodeposition solution and a known volume fraction of the electroless plating bath, and for at least two calibration solutions containing known concentrations of the reducing agent in the electrodeposition solution. One of the calibration solutions may be the electrodeposition solution without added reducing agent. The metal electrodeposited from the electrodeposition solution may be the same metal as the electrolessly deposited metal or may be a different metal. The reducing agent concentration in the electroless plating bath is determined by comparing the metal electrodeposition rate for the test solution with the metal electrodeposition rate measured for the calibration solutions.

In a preferred embodiment, the concentration of a reducing agent in a plating bath for electroless plating of a first metal is determined from the increase produced by the reducing agent in the electrodeposition rate of a second metal in an electrodeposition solution. A calibration curve is generated by measuring an electrodeposition rate parameter for the second metal in the electrodeposition solution containing known concentrations of the reducing agent. Two calibration solutions are needed, one of which may be the electrodeposition solution without reducing agent. For the reducing agent analysis, the electrodeposition rate parameter is measured for a test solution containing a known volume fraction of the plating bath sample added to the electrodeposition solution, which may initially contain no reducing agent or a relatively small concentration of reducing agent. Preferably, the rate parameters for the calibrations and the reducing agent analysis are normalized with respect to the electrodeposition rate parameter for the electrodeposition solution containing little or no reducing agent. Metal electrodeposition rates are preferably determined from the current or charge associated with voltammetric plating and stripping of the second metal at a rotating disk electrode comprised of an inert metal (e.g., platinum). In this case, the electrodeposition solution is chosen to provide reversible electrodeposition of the second metal.

The method of the present invention is particularly useful for measuring the concentration of reducing agents in electroless cobalt and nickel baths of the type used for depositing barrier layers for Damascene copper circuits, for example. In a preferred approach, measurements of the copper electrodeposition rate in an acid copper sulfate electrodeposition solution (preferably without organic additives) are used to determine the concentration of the reducing agent in the electroless cobalt or nickel plating bath. A preferred electrodeposition rate parameter is the CVS peak area ($A_r$) measured at a platinum disk electrode rotating at constant rate. This approach may also be used to measure the reducing agent concentration for cobalt and nickel electroless plating baths involving co-deposition of other metals (tungsten, molybdenum or rhenium, for example).

The method of the present invention may also be used to measure the concentrations of individual reducing agents in electroless plating baths employing more than one reducing agent. For example, hypophosphite and dimethylaminoborane (DMAB) reducing agents in electroless cobalt and nickel baths may be analyzed by taking advantage of the instability of DMAB (compared to hypophosphite) in acidic solutions.

The present invention provides an analysis method that enables reducing agents in electroless plating baths to be analyzed and controlled so as to ensure acceptable metal deposits. This method requires relatively few chemical reagents, avoids the complicated procedures of prior art methods, and can be performed rapidly, which enables close process control. The only sample preparation needed is dilution with de-ionized water or a predetermined solution (an acidic solution, for example). The method may be used for analysis of electroless plating baths for deposition of a variety of metals and alloys, including those which tend to form passive oxide layers.

Further features and advantages of the invention will be apparent to those skilled in the art from the following detailed description, taken together with the accompanying drawings.

DETAILED DESCRIPTION OF THE INVENTION

Figure 1:
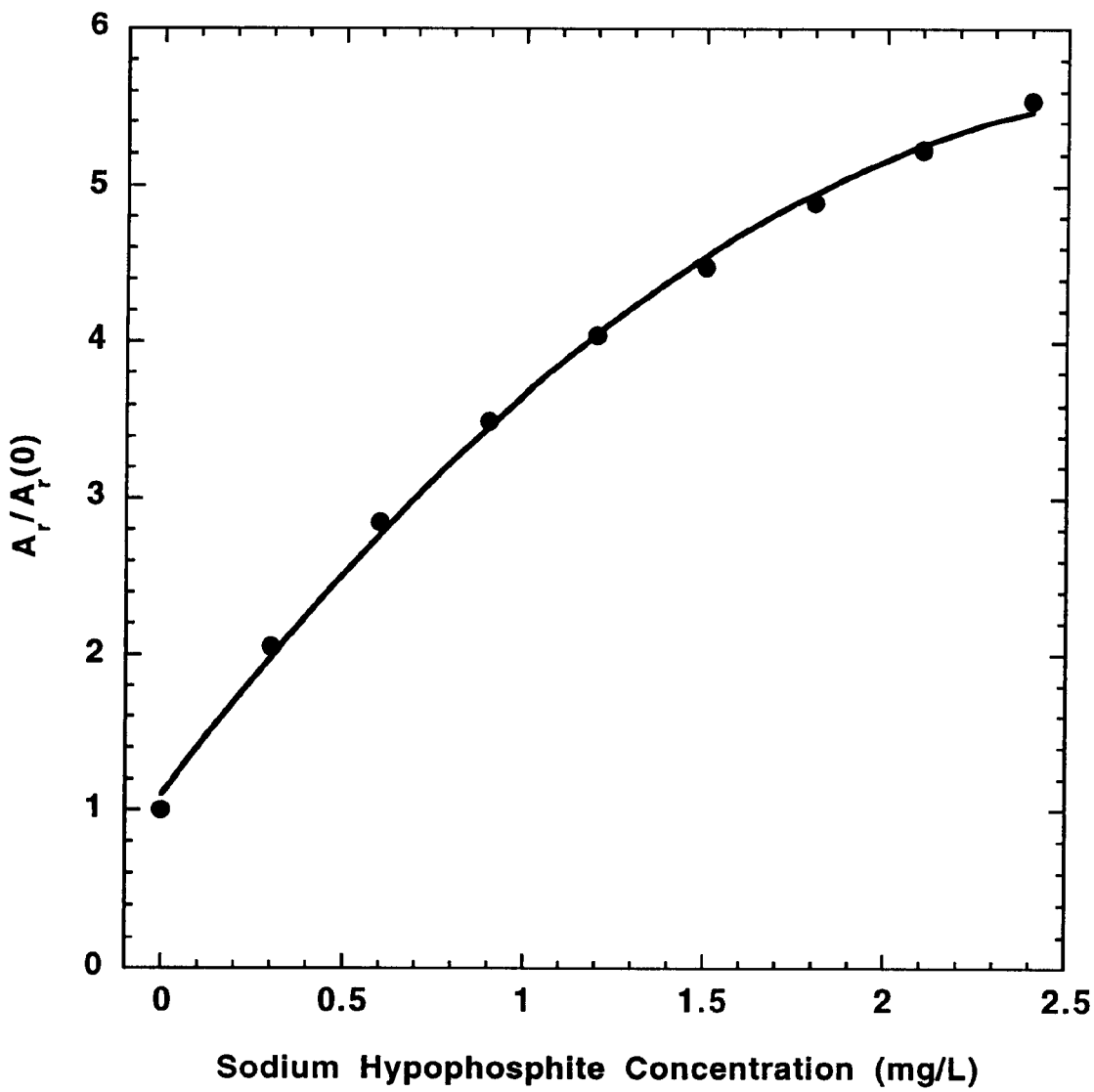
FIG. 1 shows a calibration plot of the CVS normalized copper stripping peak area as a function of the sodium hypophosphite concentration in an acid copper electrodeposition solution.

Technical terms used in this document are generally known to those skilled in the art. The term "electrode potential", or simply "potential", refers to the voltage occurring across a single electrode-electrolyte interface. In practice, the electrode potential often includes an appreciable resistive voltage drop in the electrolyte, which typically remains constant and does not affect voltammetric analysis results. As used in this document, the terms "plating" and "deposition" are equivalent, as are the terms "electroplating" and "electrodeposition" The symbol "M" means molar concentration.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

In this document, the term "standard addition" generally means addition of a known volume of an electroless plating bath sample to a known volume of an electrodeposition solution. The volume fraction is the volume of the electroless bath sample divided by the total volume of the solution after addition of the bath sample. The term "standard addition" also encompasses addition of a known weight of a solid reducing agent to a known volume of an electrodeposition solution. In addition, calibration data are typically handled as calibration curves or plots but such data may be tabulated and used directly, especially by a computer, and the terms "curve" or "plot" used in this document include tabulated data.

The present invention provides a method for determining the concentration of a reducing agent in an electroless plating bath from the increase produced by the reducing agent in the electrodeposition rate of a metal. The method may be applied to a variety of electroless plating baths, including those used for deposition of cobalt, nickel, copper, gold, palladium and platinum, as well as those involving co-deposition of other metals, for example, co-deposition of tungsten, molybdenum or rhenium with cobalt or nickel. The method does not depend directly on the chemical nature of the reducing agent and may be used for analysis of a wide variety of reducing agents, including hypophosphite, borohydride, cyanoborohydride, hydrazine, formaldehyde, formate, glyoxylic acid, hydroxylamine hydrochloride, and various boranes, including dimethylamineborane and triethyleneborane. The metal electrodeposition rate is preferably determined by cyclic voltammetric stripping (CVS) or cyclic pulse voltammetric stripping (CPVS). The latter is also called cyclic step voltammetric stripping (CSVS). As used in this document, the term "cyclic voltammetric stripping" or "CVS" implicitly includes the CPVS method, which is a variation of the CVS method. Likewise, the term "CVS rate parameter" includes the analogous CPVS voltammetric rate parameters.

In the CVS method, the potential of an inert working electrode, typically platinum, is cycled in a metal electrodeposition solution at a constant rate between fixed potential limits so that the metal is alternately electrodeposited on the electrode surface and anodically stripped back into the solution. Preferably, a rotating disk electrode configuration is used for the working electrode to control solution mass transport so as to improve the sensitivity and reproducibility of the analysis results. The metal deposition rate is preferably measured via the metal stripping peak area at a constant electrode rotation rate ($A_r$) but may also be determined from the stripping peak height, or from the electrode impedance, current (including average current), or integrated current (charge) measured for a predetermined cathodic potential or potential range (with or without electrode rotation). All of these rate parameters provide a relative measure of the metal electrodeposition rate that can readily be used for comparisons only when the measurement conditions are the same.

Improved reproducibility and accuracy for the reducing agent analysis may be provided by using a normalized electrodeposition rate parameter, such as the ratio of the rate parameter for the test or calibration solution to that for the electrodeposition solution containing little or no reducing agent. The electrodeposition rate parameter for the test and calibration solutions may also be normalized by other procedures, for example, via the mathematical difference with respect to the electrodeposition rate parameter measured for the electrodeposition solution containing little or no reducing agent. Improved reproducibility and accuracy for the measured electrodeposition rate parameter may also be provided by adjusting the measurement conditions so that the electrodeposition rate in the absence of the reducing agent is substantially zero. In this case, the negative potential sweep limit for CVS analysis, or a metal electrodeposition potential for CPVS analysis, is preferably predetermined to be just positive of the potential at which the metal is electrodeposited at an appreciable rate (as indicated by a substantial $A_r$ value) in the absence of the reducing agent.

For CVS electrodeposition rate measurements, a plurality of potential cycles is typically employed to condition the working electrode surface so as to provide reproducible results. Electrode conditioning may be performed for a predetermined number of cycles (3 cycles, for example), or until a steady-state electrode condition is indicated by substantially equivalent voltammograms or voltammetric features on successive cycles. Typically, steady state is indicated by successive $A_r$ values that differ by less than a predetermined percentage (0.5%, for example).

The inert working electrode for CVS measurements may be comprised of any suitable electrically conducting material that is stable in the electrodeposition solution under the conditions used for the voltammetric analysis but is preferably comprised of a noble metal, for example, platinum, iridium, gold, osmium, palladium, rhenium, rhodium, ruthenium, and alloys thereof. Other oxidation-resistant metals and alloys, stainless steel, for example, may also be used as working electrode materials. A typical CVS rotating disk electrode is comprised of a platinum metal disk (3–5 mm diameter), with an electrical contact wire on the backside, embedded flush with one end of an insulating plastic cylinder (10–20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). The rotating disk electrode is usually rotated at a constant rate (100–10,000 rpm) but the electrode rotation may be modulated with time.

Precise control over the working electrode potential needed for CVS measurements is typically provided via an electronic potentiostat in conjunction with a counter electrode and a reference electrode, e.g., silver-silver chloride (SSCE), mercury-mercury sulfate, or saturated calomel electrode (SCE). A double junction may be used to extend the life of the reference electrode by inhibiting intrusion of plating bath species. The counter electrode is typically comprised of the same metal as the metal deposited on the working electrode but an inert metal may also be employed. Depolarizers (sulfur or phosphorus, for example) may be included in the counter electrode to facilitate dissolution of the metal so as to avoid breakdown of the electrodeposition solution. Practically any electrical conductor that resists oxidation and reduction in the electrodeposition solution may be used as an inert counter electrode, including metals, alloys and conducting oxides (mixed titanium-ruthenium oxide, for example). A preferred inert counter electrode material is 316 stainless steel, which is highly oxidation-resistant and relatively inexpensive, but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

Metal electrodeposition rates according to the present invention may also be measured by methods other than CVS, including those based on measurements of the ac impedance of the cathode, for example. The same electrode materials and configurations may be used for such alternative methods. Although the precision and reproducibility of the analysis might be degraded, current measurements reflecting the metal electrodeposition rate could also be made at a stationary electrode and/or without potential cycling. If a stationary working electrode is used for reducing agent analysis of the present invention, the hydrodynamic conditions at the electrode surface are preferably controlled, by stirring or pumping the solution, for example.

For the reducing agent analysis of the present invention, the electrolessly deposited metal and the electrodeposited metal may be the same metal. In this case, the electrodeposition rate parameter is measured for a test solution comprised of an electrodeposition solution and a sample of the electroless plating bath, which may be diluted with de-ionized water or an electrolytic solution. This approach has the disadvantage that the electrodeposition rate for metals tending to form passive oxide layers, such as cobalt and nickel, cannot readily be determined by voltammetric stripping.

In a preferred embodiment, the concentration of a reducing agent in an electroless plating bath for deposition of a first metal is determined from the increase produced by the reducing agent in the electrodeposition rate of a second metal in an electrodeposition solution. Preferably, the second metal is substantially more noble than the first metal in the sense that ions of the second metal tend to be more easily reduced in aqueous solutions. In this case, a given concentration of the relatively powerful reducing agent required to reduce ions of the first metal will produce a relatively large increase in the electrodeposition rate of the second metal (at a given electrode potential). Preferably, the second metal is reversibly electrodeposited so that the electrodeposition rate can be readily measured by CVS or CPVS analysis. Metals that tend to undergo reversible electrodeposition include copper, silver, tin, indium, lead, zinc, bismuth and cadmium. The second metal may also be an alloy, and the alloy may include metals for which electrodeposition of the pure metal is irreversible. Preferably, organic additives typically used in electroplating baths to brighten and level deposits are not added to the electrodeposition solution since they generally affect the metal electrodeposition rate and would tend to interfere with the reducing agent analysis. Surfactants and other organic additives that do not substantially affect the electrodeposition rate may be included in the electrodeposition solution.

A preferred electrodeposition solution for the analysis of the present invention is acid copper sulfate without organic additives. A wide range of acid copper compositions may be used. Typical ranges for acid copper sulfate baths, which may be suitable for the analysis of the present invention, are 40–200 g/L copper sulfate pentahydrate, 1–350 g/L sulfuric acid, and 25–100 mg/L chloride ion. Constituents of the electroless plating bath, such as complexing agents, may be included in the electrodeposition solution to minimize interference with the reducing agent analysis. In some cases, a small concentration of the reducing agent to be analyzed may be included in the baseline electrodeposition solution to adjust the response range and improve the consistency of the analysis results. Copper electrodeposition solutions based on other anions may also be used. Alternative anions include pyrophosphate, sulfamate, citrate, chloride, bromide, iodide, fluoroborate, alkylsulfonate, and mixtures thereof.

For analysis of reducing agents in electroless cobalt and nickel baths containing citrate as a complexing agent, a preferred acid copper electrodeposition solution contains 70 g/L copper sulfate pentahydrate, 175 g/L sulfuric acid, 50 mg/L chloride ion, and 1 g/L sodium citrate dihydrate. Inclusion of citrate in the electrodeposition solution minimizes interference of citrate derived from standard addition of the electroless bath sample to the electrodeposition solution. Since the electroless plating bath sample is typically diluted before and during addition to the electrodeposition solution, the concentration of citrate included in the electrodeposition solution should be concomitantly small.

Improved results for the analysis of the present invention may be provided by optimizing the CVS measurement parameters. The key CVS measurement parameters and their typical ranges for acid copper systems include the electrode rotation rate (100 to 10,000 rpm), potential scan rate (10 to 1000 mV/s), negative potential limit (−0.05 to −0.5 V vs. SSCE) and positive potential limit (1.4 to 1.8 V vs. SSCE). In a preferred embodiment, the negative potential sweep limit for CVS analysis, or a metal electrodeposition potential for CPVS analysis, is predetermined to be just positive of the potential at which the $A_r$ value becomes substantially measurable. This potential is typically about 0.0 V vs. SSCE for acid copper electrodeposition solutions. In another preferred embodiment, the negative potential sweep limit for CVS analysis, or a metal electrodeposition potential for CPVS analysis, is predetermined to provide a substantial $A_r$ value that is readily measurable and reproducible. A positive potential limit of relatively high voltage (in the oxygen evolution region) is typically used so that contaminants adsorbed on the electrode surface are removed by electrochemical oxidation on each cycle, which provides more reproducible results. Additional CPVS measurement parameters include the potentials and hold times for the pulses or steps used. The accuracy of the electrodeposition rate measurement may be improved by employing a slightly elevated solution temperature (typically, 3° or 4° C. above room temperature), which can be more consistently maintained.

The method of the present invention is particularly useful for measuring the concentration of reducing agents in electroless cobalt and nickel baths, including those from which other metals (tungsten, molybdenum or rhenium, for example) are co-deposited. Cobalt and nickel tend to form a passive surface oxide layer so that plating and stripping of these metals cannot readily be used to measure the electrodeposition rate. In a preferred approach, measurements of the copper electrodeposition rate in an acid copper sulfate electrodeposition solution (without organic additives) are used to determine the concentration of the reducing agent in electroless cobalt and nickel plating baths. A preferred electrodeposition rate parameter is the CVS stripping peak area ($A_r$) measured at a platinum disk electrode rotating at constant rate. The $A_r$ value is determined for a test solution comprised of the acid copper electrodeposition solution and a known volume fraction of the electroless cobalt or nickel bath, and for the copper electrodeposition solution alone, termed $A_r(0)$. The reducing agent concentration is determined by comparing $A_r$ or the normalized rate parameter $A_r/A_r(0)$ for the test solution with a calibration curve of $A_r$ or $A_r/A_r(0)$ as a function of the concentration of the reducing agent in the acid copper electrodeposition solution. Alternative normalized rate parameters, $A_r$–$A_r(0)$, for example, may also be used.

Since small amounts of the reducing agent usually have a strong effect on the metal electrodeposition rate, the electroless plating bath sample is typically diluted prior to addition to the electrodeposition solution. The bath sample may be diluted with de-ionized water or a solution, for example, the electrodeposition solution or a solution containing one or more of constituents of the plating bath or the electrodeposition solution. Dilution with an acidic solution (sulfuric acid, for example) may be used to minimize matrix effects (for an acid copper sulfate bath, for example) or to decompose species (other reducing agents, for example) that would interfere with the analysis. Such dilution provides optimum sensitivity to the reducing agent concentration and minimizes errors associated with solution handling. For analysis of electroless cobalt or nickel baths, the bath sample is typically diluted by a ratio of 1:100 before addition to the electrodeposition solution. Further dilution of the reducing agent results from standard addition of the diluted bath sample to the electrodeposition solution.

The effects of other constituents of the electroless bath on the reducing agent analysis are usually not significant since the volume fraction of electroless plating bath sample added to the electrodeposition solution is typically small. Ions of less noble metals (including cobalt, nickel, tungsten, molybdenum and rhenium) in electroless baths typically do not interfere with the reducing agent analysis since such metals do not readily co-deposit with relatively noble metals (such as copper), especially from solutions without organic brightening or leveling additives. The effects of constituents of the electroless plating bath that may affect the metal electrodeposition rate even at low concentrations (complexing agents, for example) may be minimized by including such constituents in the electrodeposition solution.

The method of the present invention may also be used to measure the concentrations of individual reducing agents in electroless plating baths employing more than one reducing agent. For example, hypophosphite and dimethylaminoborane (DMAB) reducing agents in electroless cobalt and nickel baths may be analyzed by taking advantage of the instability of DMAB (compared to hypophosphite) in acidic solutions. In this case, the electroless plating bath sample is diluted by addition to an acidic solution (sulfuric acid, for example) that decomposes the DMAB reducing agent via the reaction:

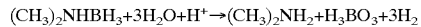

which involves evolution of hydrogen gas. Sufficient time is allowed for substantially complete decomposition of the DMAB reducing agent, which is indicated by cessation of hydrogen gas bubble formation. The concentration of hypophosphite, which is stable in acidic solutions, is then determined from the change in the metal electrodeposition rate produced by standard addition of the acidic solution (containing the diluted bath sample) to a metal electrodeposition solution, preferably acid copper sulfate solution.

The DMBA reducing agent concentration in an electroless cobalt or nickel bath also containing hypophosphite reducing agent may be determined by a conventional titration method. In this case, the DMBA in an electroless plating bath sample is first fully oxidized in an acidic solution by addition of excess iodine, which is then back-titrated with a solution containing thiosulfate ion as a reducing agent. The endpoint may be determined potentiometrically or colorometrically (loss of the iodine brown color in solution). Hypophosphite is not oxidized by iodine so that it does not interfere with the DMAB analysis.

Alternatively, the DMBA reducing agent concentration in an electroless cobalt or nickel bath also containing hypophosphite reducing agent may be determined by the method of the present invention. A preferred approach is to measure the copper electrodeposition rate in an acid copper electrodeposition solution (containing sulfuric acid) before and immediately after standard addition of an electroless plating bath sample (typically diluted with de-ionized water), and after a time delay sufficient to allow substantially complete decomposition of the DMBA reducing agent. The electrodeposition rate after the time delay provides a measure of the hypophosphite concentration in the electroless plating bath. After subtraction of the increase in the electrodeposition rate produced by hypophosphite, the electrodeposition rate immediately after the standard addition provides a measure of the DMAB concentration in the electroless plating bath. Errors in the DMAB analysis associated with decomposition of DMAB prior to the immediate electrodeposition rate measurement can be minimized by utilizing an acid copper electrodeposition solution with relatively low sulfuric acid concentration. Alternatively, a nearly neutral electrodeposition solution (pH 8 copper pyrophosphate, for example) or one of relatively low acidity (pH 3 copper sulfamate, for example) may be used to minimize decomposition of DMAB prior to the electrodeposition rate measurement used for the DMAB analysis. In this case, the electroless plating bath sample would be diluted with acid solution (to decompose DMAB) for the hypophosphite analysis and with de-ionized water for the DMAB analysis.

In practice, a calibration curve is typically generated by measuring a predetermined metal electrodeposition rate parameter in a predetermined electrodeposition solution, initially and after each standard addition of the reducing agent. For the reducing agent analysis, a sample of the electroless plating bath is usually diluted with de-ionized water or a predetermined solution, and the electrodeposition rate parameter is measured in the electrodeposition solution before and after standard addition of the diluted plating bath sample. The reducing agent concentration in the electroless plating bath sample is determined from the measured electrodeposition rate parameter by interpolation with respect to the calibration curve. When the electroless plating bath contains a first reducing agent that is stable in acidic solution and a second reducing agent that is unstable in acidic solution, a separate calibration curve is generated (by standard addition) for each reducing agent. The bath sample used for analysis of the first reducing agent is diluted with an acidic solution and time is allowed for the second reducing agent to decompose before the standard addition to the electrodeposition solution.

Within the scope of the present invention, variations in the analysis procedures and data handling will be apparent to those skilled in the art. For example, the reducing agent concentration may be determined by linear approximation analysis. In this case, a metal electrodeposition rate parameter (e.g., $A_r$) is measured for the electrodeposition solution before and after addition of a known volume fraction of the electroless plating bath. The electrodeposition rate parameter measurement is then repeated in this mixed solution after one or more standard additions of the reducing agent. The concentration of the reducing agent in the electroless plating bath sample is calculated assuming that the electrodeposition rate parameter varies linearly with reducing agent concentration, which is verified if the changes in the rate parameter produced by standard additions of the same amount of reducing agent are equivalent. In this case, standard addition of the reducing agent to the test solution yields a calibration solution so that a separate calibration curve is not needed. An analogous procedure may be used when the variation in the electrodeposition rate parameter with reducing agent concentration is non-linear but is nonetheless mathematically predictable.

DESCRIPTION OF A PREFERRED EMBODIMENT

In a preferred embodiment of the present invention, the concentrations of hypophosphite and dimethylamineborane (DMAB) reducing agents in electroless cobalt and nickel plating baths are determined from the effects of standard additions of the electroless plating bath and the reducing agents on the CVS stripping peak area ($A_r$) measured at a rotating Pt disk electrode in an acid copper sulfate electrodeposition solution. For $A_r$ measurements, the electrode potential is either cycled at a constant rate between fixed positive and negative limits, or is biased at a fixed negative potential and then scanned in the positive direction at a constant rate to strip copper deposited during a predetermined time at the fixed negative potential. The negative voltage limit or the fixed negative potential is preferably predetermined to be just positive of the potential at which copper is electrodeposited at a substantial rate in the absence of reducing agent additions to the electrodeposition solution. Alternatively, the negative voltage limit or the fixed negative potential is predetermined to provide a substantial $A_r$ value that is readily measurable and reproducible. Typical ranges for the other CVS measurement parameters are 100–10,000 rpm for the electrode rotation rate, 50–500 mV/s for the potential scan rate, and 1.4 to 1.8 V vs. SSCE for the positive potential limit. The potential of the rotating disk electrode is preferably controlled relative to a reference electrode via a potentiostat and a counter electrode.

Prior to the reducing agent analysis, the potential of the working electrode is preferably cycled (over the potential range used for the analysis) in the electrodeposition solution (without reducing agents or with only a small reducing agent concentration) to condition the electrode surface. For both the electrode conditioning and the reducing agent analysis, the potential of the working electrode is preferably cycled for a predetermined number of cycles, typically three. Alternatively, the potential of the working electrode is cycled until successive $A_r$ values differ by less than a predetermined percentage (typically 0.5%).

For the reducing agent analysis, the concentrations of other constituents in the electroless plating bath are typically maintained within the ranges recommended by the bath supplier but this is not essential. After each standard addition, sufficient time should be allowed for stirring via the rotating disk electrode (or other means) to provide a homogeneous solution. During measurements, the solution temperature should be maintained at a constant value (within ±0.5° C.) around room temperature.

The efficacy of the present invention was demonstrated via CVS measurements of $A_r$ at a platinum disk electrode (4 mm diameter) rotating at 2500 rpm in an acid copper sulfate electrodeposition solution (25° C.) containing 70 g/L copper sulfate pentahydrate, 175 g/L sulfuric acid, 1 g/L sodium citrate dihydrate, and 50 mg/L chloride ion (added as hydrochloric acid). Electrolytes were prepared using de-ionized water. CVS measurements were made under potentiostatic control using a Qualilab QL-10 plating bath analyzer (ECI Technology, Inc.). The counter electrode was a stainless steel rod and the reference electrode was a modified silver-silver chloride electrode (SSCE-M) for which the solution in a standard SSCE electrode was replaced with a saturated AgCl solution also containing 0.1 M KCl and 10 volume% sulfuric acid. The working electrode potential was scanned at 300 mV/s between a positive limit of +1.575 V and a negative limit of 0.000 V vs. SSCE-M. For $A_r$ and $A_r(0)$ measurements, the anodic current was integrated from the zero-current potential (at the cathodic-anodic crossover) to 0.30 V vs. SSCE-M. The electrode was conditioned for two potential cycles; $A_r$ or $A_r(0)$ was recorded for the third cycle. During CVS measurements, the solution temperature was controlled at 25° C. within ±0.5° C.

FIG. 1 shows a calibration plot of $A_r/A_r(0)$ for the acid copper electrodeposition solution as a function of the concentration of added sodium hypophosphite ($NaH_2PO_2$). Good sensitivity to the hypophosphite concentration is evident. This calibration plot was shown to be valid for analysis of proprietary cobalt-tungsten (citrate) electroless plating baths employing the hypophosphite reducing agent alone, and those employing both hypophosphite and DMAB reducing agents. For analysis of hypophosphite in baths employing only the hypophosphite reducing agent, the bath sample was diluted 1:100 with de-ionized water and from 2 to 10 mL/L of the diluted bath sample were added to the electrodeposition solution. For analysis of hypophosphite in baths employing both hypophosphite and DMAB reducing agents, the bath sample was diluted 1:100 with 10 volume% sulfuric acid solution, two minutes were allowed for substantially complete DMAB decomposition, and then from 2 to 10 mL/L of the diluted bath sample were added to the electrodeposition solution.

Table 1 summarizes the results for analysis of samples of a proprietary cobalt-tun (citrate) electroless plating bath to which various concentrations of sodium hypophosphite ($NaH_2PO_2$), and double those concentrations of DMAB, were added. The analysis results are the averages for three runs. Good accuracy for the hypophosphite analysis is evident.

TABLE 1

Added and Analyzed Sodium Hypophosphite Concentrations

| Added (g/L) | Analyzed (g/L) |
|---|---|
| 2.89 | 2.83 |
| 3.21 | 3.17 |
| 3.53 | 3.42 |

Figure 2:
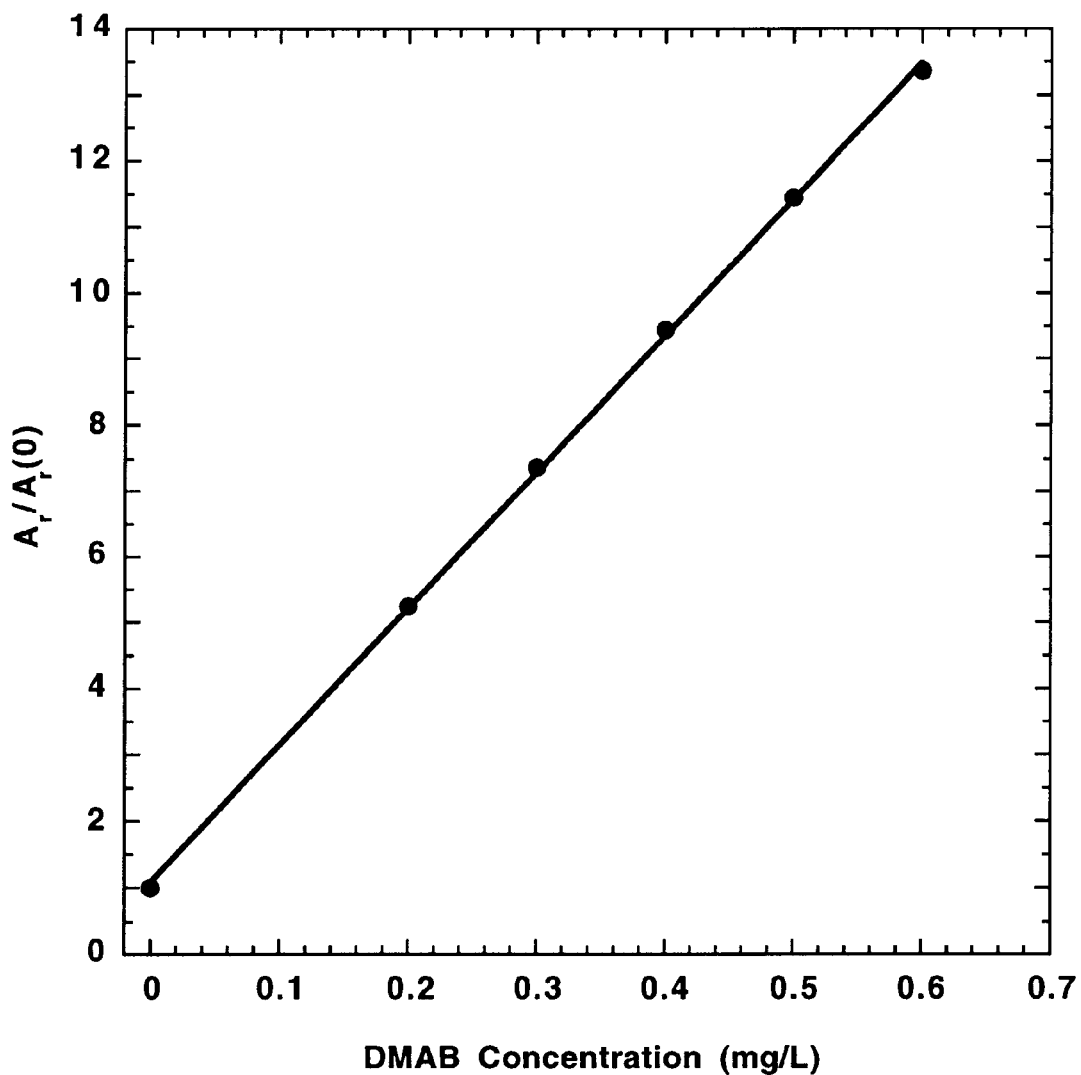
FIG. 2 shows a calibration plot of the CVS normalized copper stripping peak area as a function of the DMAB concentration in the acid copper electrodeposition solution of FIG. 1.

FIG. 2 shows a calibration plot of $A_r/A_r(0)$ for the acid copper electrodeposition solution as a function of the DMBA concentration. Good sensitivity to the DMBA concentration is evident.

Calibration and measurement according to the present invention can be performed within about 20 minutes. The analysis itself requires only about 5 minutes.

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for determining the concentration of a reducing agent in an electroless plating bath for deposition of a first metal, comprising the steps of:
    measuring an electrodeposition rate parameter for electrodeposition of a second metal from an electrodeposition solution;
    measuring the electrodeposition rate parameter for electrodeposition of the second metal from a test solution comprising the electrodeposition solution and a known volume fraction of the electroless plating bath;
    measuring the electrodeposition rate parameter for electrodeposition of the second metal from a calibration solution comprising the electrodeposition solution and a known concentration of the reducing agent; and
    comparing the electrodeposition rate parameters for the electrodeposition solution, the test solution, and the calibration solution to determine the concentration of the reducing agent in the electroless plating bath.

2. The method of claim 1, wherein the reducing agent is selected from the group consisting of hypophosphite, dimethylamineborane, triethyleneborane, borohydride, cyanoborohydride, hydrazine, formaldehyde, formate, glyoxylic acid, and hydroxylamine hydrochloride.

3. The method of claim 1, wherein the first metal is selected from the group consisting of cobalt, nickel, molybdenum, tungsten, rhenium, copper, gold, palladium, platinum and alloys thereof.

4. The method of claim 1, wherein the electrodeposition rate parameter is measured by a method selected from the group consisting of CVS and CPVS.

5. The method of claim 4, wherein the electrodeposition rate parameter is selected from the group consisting of stripping peak area, stripping peak height, current at a predetermined cathodic potential, integrated current over a predetermined cathodic potential range, and average current over a predetermined cathodic potential range.

6. The method of claim 1, wherein the electrodeposition rate parameter is measured by an alternating current (ac) method.

7. The method of claim 1, wherein the electrodeposition rate parameter is a normalized electrodeposition rate parameter.

8. The method of claim 1, wherein the electrodeposition solution contains the reducing agent at a predetermined concentration.

9. The method of claim 1, wherein the first metal and the second metal are the same metal.

10. The method of claim 1, wherein the second metal is selected from the group consisting of copper, silver, tin, indium, lead, zinc, bismuth, cadmium, and alloys thereof.

11. The method of claim 1, wherein the electrodeposition solution includes anions selected from the group consisting of sulfate, pyrophosphate, sulfamate, citrate, chloride, bromide, iodide, fluoroborate, alkylsulfonate, and mixtures thereof.

12. The method of claim 1, wherein the electrodeposition solution includes a complexing agent which is also present in the electroless plating bath.

13. A method for determining the concentration of a reducing agent in an electroless plating bath for deposition of a first metal, comprising the steps of:
    measuring an electrodeposition rate parameter for electrodeposition of copper from an electrodeposition solution;
    measuring the electrodeposition rate parameter for electrodeposition of copper from a test solution comprising the electrodeposition solution and a known volume fraction of the electroless plating bath;
    measuring the electrodeposition rate parameter for electrodeposition of copper from a calibration solution comprising the electrodeposition solution and a known concentration of the reducing agent; and
    comparing the electrodeposition rate parameters for the electrodeposition solution, the test solution, and the calibration solution to determine the concentration of the reducing agent in the electroless plating bath.

14. The method of claim 13, wherein the reducing agent is selected from the group consisting of hypophosphite, dimethylamineborane, borohydride, and hydrazine.

15. The method of claim 13, wherein the first metal is selected from the group consisting of cobalt, nickel, molybdenum, tungsten, rhenium, and alloys thereof.

16. The method of claim 13, wherein the electrodeposition rate parameter is measured by a method selected from the group consisting of CVS and CPVS.

17. The method of claim 16, wherein the electrodeposition rate parameter is selected from the group consisting of stripping peak area, stripping peak height, current at a predetermined cathodic potential, integrated current over a predetermined cathodic potential range, and average current over a predetermined cathodic potential range.

18. The method of claim 13, wherein the electrodeposition rate parameter is measured by an alternating current (ac) method.

19. The method of claim 13, wherein the electrodeposition rate parameter is a normalized electrodeposition rate parameter.

20. The method of claim 13, wherein the electrodeposition solution contains the reducing agent at a predetermined concentration.

21. The method of claim 13, wherein the electrodeposition solution includes anions selected from the group consisting of sulfate, pyrophosphate, sulfamate, citrate, chloride, bromide, iodide, fluoroborate, alkylsulfonate, and mixtures thereof.

22. The method of claim 13, wherein the electrodeposition solution includes a complexing agent which is also present in the electroless plating bath.

23. A method for determining the concentration of a reducing agent in an electroless cobalt plating bath, comprising the steps of:

measuring the cyclic voltammetric stripping $A_r$ parameter for an acid copper electrodeposition solution;

measuring the $A_r$ parameter for a test solution comprising the acid copper electrodeposition solution and a known volume fraction of the electroless cobalt plating bath;

measuring the $A_r$ parameter for a calibration solution comprising the acid copper electrodeposition solution and a known concentration of the reducing agent; and comparing the $A_r$ parameters for the copper electrodeposition solution, the test solution, and the calibration solution to determine the concentration of the reducing agent in the electroless cobalt plating bath.

24. The method of claim 23, wherein the reducing agent is selected from the group consisting of hypophosphite, dimethylamineborane, borohydride, and hydrazine.

25. The method of claim 23, wherein the electroless cobalt plating bath includes ions of a metal selected from the group consisting of molybdenum, tungsten, and rhenium.

26. A method for determining the concentration of a reducing agent in an electroless nickel plating bath, comprising the steps of:

measuring the cyclic voltammetric stripping $A_r$ parameter for an acid copper electrodeposition solution;

measuring the $A_r$ parameter for a test solution comprising the acid copper electrodeposition solution and a known volume fraction of the electroless nickel plating bath;

measuring the $A_r$ parameter for a calibration solution comprising the acid copper electrodeposition solution and a known concentration of the reducing agent; and comparing the $A_r$ parameters for the copper electrodeposition solution, the test solution, and the calibration solution to determine the concentration of the reducing agent in the electroless nickel plating bath.

27. The method of claim 26, wherein the reducing agent is selected from the group consisting of hypophosphite, dimethylamineborane, borohydride, and hydrazine.

28. The method of claim 26, wherein the electroless nickel plating bath includes ions of a metal selected from the group consisting of molybdenum, tungsten, and rhenium.

* * * * *